US010883126B2

(12) United States Patent
Thongchul et al.

(10) Patent No.: US 10,883,126 B2
(45) Date of Patent: Jan. 5, 2021

(54) **PROCESS FOR PRODUCING LACTIC ACID OR ITS SALTS FROM FERMENTATION USING THERMOTOLERANCE *BACILLUS* BACTERIA**

(71) Applicants:PTT Global Chemical Public Company Limited, Chatuchak Bangkok (TH); Chulalongkorn University, Bangkok (TH)

(72) Inventors: Nuttha Thongchul, Bangkok (TH); Vasana Tolieng, Bangkok (TH); Phatthanon Prasitchoke, Bangkok (TH)

(73) Assignee: PTT GLOBAL CHEMICAL PUBLIC COMPANY LIMITED

( * ) Notice: Subject to any disclaimer, the term of this patent is extended or adjusted under 35 U.S.C. 154(b) by 268 days.

(21) Appl. No.: 15/738,888

(22) PCT Filed: Jun. 28, 2016

(86) PCT No.: PCT/TH2016/000058
§ 371 (c)(1),
(2) Date: Dec. 21, 2017

(87) PCT Pub. No.: WO2017/003387
PCT Pub. Date: Jan. 5, 2017

(65) Prior Publication Data
US 2019/0100779 A1 Apr. 4, 2019
US 2020/0199633 A2 Jun. 25, 2020

(30) Foreign Application Priority Data

Jun. 29, 2015 (TH) ............................... 1501003766

(51) Int. Cl.
*C12P 7/56* (2006.01)
*C12R 1/07* (2006.01)
*C12N 1/22* (2006.01)

(52) U.S. Cl.
CPC ................ *C12P 7/56* (2013.01); *C12N 1/22* (2013.01); *C12R 1/07* (2013.01)

(58) Field of Classification Search
CPC .. C12P 7/56; C12N 1/22; A01N 63/22; C12R 1/07; Y10S 435/801
See application file for complete search history.

(56) References Cited

U.S. PATENT DOCUMENTS

| 5,002,881 | A | 3/1991 | Van Nispen et al. |
| 8,119,376 | B2 | 2/2012 | Otto |
| 8,445,239 | B2 * | 5/2013 | Costantino ............ C08B 37/006 435/101 |
| 2004/0029238 | A1 | 2/2004 | Rajgarhia et al. |
| 2013/0143286 | A1 | 6/2013 | Xu et al. |
| 2013/0171705 | A1 * | 7/2013 | Sonomoto ................ C12P 7/56 435/139 |

FOREIGN PATENT DOCUMENTS

| WO | 2006124633 A1 | 11/2006 |
| WO | 2014081395 A1 | 5/2014 |
| WO | WO-2014081395 A1 * | 5/2014 |

OTHER PUBLICATIONS

Endres, J.R. et al., Safety Assessment of a Proprietary Preparation of a Novel Probiotic, Bacillus Coagulans, As a Food Ingredient, 2009,Food and Chemical Toxicology, vol. 47, pp. 1231-1238. (Year: 2019).*
Qin et al.,"Production of L-lactic acid by a thermophilic Bacillus mutant using sodium hydroxide as neutralizing agent," Bioresource Technology, vol. 101, pp. 7570-7576 (2010).
Ouyang et al., "Efficient Non-sterilized Fermentation of Biomass-Derived Xylose to Lactic Acid by a Thermotolerant Bacillus coagulans NL01," Appl. Biochem. Biotechnol., vol. 168, pp. 2387-2397 (2012).
Wang et al., "Isolation, characterization and evolution of a new thermophilic Bacillus licheniformis for lactic acid production in mineral salts medium," Bioresource Technology, vol. 102, pp. 8152-8158 (2011).
Ye et al., Highly efficient production of L-lactic acid from xylose by newly isolated Bacillus coagulans C106, Bioresource Technology, vol. 132, pp. 38-44 (2013).
Written Opinion of the International Searching Authority dated May 2, 2017.
International Search Report for PCT/TH2016/000058 dated May 2, 2017.

* cited by examiner

*Primary Examiner* — Thane Underdahl
(74) *Attorney, Agent, or Firm* — Kim IP Law Group LLC

(57) ABSTRACT

This invention relates to a process for producing lactic acid or its salts that can be performed easily, reduce complicated steps, and provide high lactic acid yield and high productivity, wherein said process comprising of the following steps: (a) cultivating thermotolerance *Bacillus* genus bacteria to obtain a seed culture; (b) increasing cell number of bacteria by inoculating the seed culture contained from step (a) into a fermenter containing an initial carbon source under an aerobic condition; (c) fermenting the seed culture obtained from step (b) in the fermenter under a microaerobic condition to obtain lactic acid or its salts; wherein the step (b) comprising at least one addition of the carbon source under any one of the following conditions, where are independent to each other, to increase a concentration of the carbon source:
when the concentration of the carbon source in the fermenter reduces to 50 % or less comparing to the initial concentration.

38 Claims, No Drawings

PROCESS FOR PRODUCING LACTIC ACID OR ITS SALTS FROM FERMENTATION USING THERMOTOLERANCE *BACILLUS* BACTERIA

CROSS-REFERENCE TO RELATED APPLICATIONS

This application is a 371 national phase application of International Patent Application No. PCT/TH2016/000058, filed Jun. 28, 2016, which claims foreign priority to Thailand patent application no. 150103766, filed Jun. 29, 2015, the entire disclosures of which are hereby incorporated by reference herein in their entireties.

FIELD OF THE INVENTION

This invention is in the field of biotechnology relating to the fermentation process and bacteria that can produce lactic acid.

BACKGROUND OF THE INVENTION

It is well known that lactic acid is widely used in plastic industry, food and drug industry, and cosmetic industry. For plastic industry, lactic acid is widely used, especially for the production of polyester such as polylactic acid or poly (lactic-co-glycolic acid). Polymer produced from lactic acid has an advantage that it is biodegradable and biocompatible. Said polymer can be used in many applications such as fiber in textile, film, catgut packaging, and scaffold in medical.

At present, there are several production processes of lactic acid such as chemical synthesis and biotechnology. The biotechnology has several advantages, including utilization of renewable resources for microbial fermentation such as cassava, corn, wheat, or cane. Moreover, the microbial fermentation can produce lactic acid with high optical purity.

Most of lactic acid productions are the fermentation of sugar such as glucose, sucrose, maltose, or other carbohydrates such as starch or cellulose, wherein microorganisms that can produce lactic acid can be both bacteria and fungi.

Bacteria in genus *Lactobacillus, Leuconostoc,* and *Streptococcus* are well known for the production of lactic acid from sugar under an anaerobic condition, leading to energy saving and providing higher yield than the one produced by fungi. However, said bacteria genus are fastidious bacteria, which need vitamins and essential amino acids for their growth. Moreover, said bacteria genus cannot produce enzyme to convert starch into sugar, which needs the pretreatment step of converting starch to sugar prior to fermentation. This increases the production cost.

One problem of polymer production from lactic acid is high production cost. It is necessary to develop the lactic acid production process with lower production cost, high yield and high productivity. In addition, there are several attempts to develop microorganisms and culturing steps in order to produce robust microorganisms that have ability to grow and proliferate with high rate.

One attempt to reduce the lactic acid production cost is the reduction of production step such as the use of thermotolerance *Bacillus* bacteria in lactic acid production. This is because normally the raw material of lactic acid production requires a pretreatment process prior to fermentation. Several pretreatment can be used, including mechanical treatment, heat treatment, chemical treatment, or enzyme treatment, depending on the physical, chemical, and nutritional property of such carbon sources. Said pretreatment processes are generally performed at high temperature in a range from about 50 to about 100° C. General bacteria cannot grow at said temperature. Therefore, an additional step is needed to reduce the temperature to a room temperature prior to using such carbon sources in lactic acid production. This results in complication of production process and higher production cost.

Therefore, there had been developments in production process of lactic acid using thermotolerance *Bacillus* bacteria such as *Bacillus coagulans, Bacillus acidiproducens, Bacillus stearothermophilus,* and *Bacillus licheniformis* as disclosed in Ouyang et al, (Appl. Biochem. Biotechnol., 2012, 168, 2387-2397), Wang et al, (Bioresour. Technol., 2011, 102, 8152-8158), and U.S. Pat. No. 8,119,376. However, it was found that the production of lactic acid as disclosed in said documents resulted in low productivity and yield, which was the limitation for the production of lactic acid in the industrial scale.

One attempt to reduce lactic acid production cost is to eliminate the purifying step of lactic acid obtained from fermentation. The neutralizing agent is one of important factors. Generally, calcium carbonate ($CaCO_3$) that is used in the production of lactic acid generates calcium lactate as by product. Therefore, the acidification step is further needed to convert calcium lactate into lactic acid by using acid solution such as sulfuric acid ($H_2SO_4$). This contributes to the complication of production process and high production cost. Moreover, said process causes calcium sulfate ($CaSO_4$) which is the undesired by product, leading to a problem to eliminate said substance, especially in the industrial scale production.

U.S. Pat. No. 5,002,881 and WO2006124633 disclosed the use of ammonium hydroxide ($NH_4OH$) as neutralizing agent during fermentation in lactic acid production. However, ammonium hydroxide is a volatile compound which could be harmful to operator's health. Besides, ammonium hydroxide is a weak basic; thus, it is needed to be used in high amount to control pH that results in a difficulty in separation and purification steps.

Ye et al, (Bioresour. Technol., 2013, 132, 38-44), Qin et al, (Bioresour. Technol., 2010, 101, 7570-7576) disclosed the use of strong basic such as sodium hydroxide (NaOH) and potassium hydroxide (KOH) during the fermentation of lactic acid production. However, it was found that the use of said basic caused the negative effect on the bacteria cell, resulting in low productivity and yield.

From the reasons mentioned above, this invention aims to improve the process for producing lactic acid or its salt from fermentation to provide high productivity and yield, wherein said process can be performed easily and reduce complicated steps.

SUMMARY OF THE INVENTION

This invention relates to a process for producing lactic acid or its salts from fermentation using thermotolerance *Bacillus* bacteria, said process comprising the following steps:

(a) cultivating thermotolerance *Bacillus* bacteria to obtain seed culture;

(b) increasing cell number of bacteria by inoculating the seed culture obtained from step (a) into a fermenter containing an initial carbon source under an aerobic condition;

(c) fermenting the seed culture obtained from step (b) in the fermenter under a microaerobic condition to obtain lactic acid or its salts;

wherein the step (b) comprising at least one addition of the carbon source under any one of the following conditions, which are independent to each other, to increase a concentration of the carbon source:
  when the concentration of the carbon source in the fermenter reduces to 50% or less comparing to the initial concentration;
  when the step (b) is carried out for a time of at least one third;
  when an optical density (OD) of bacterial cell in the fermenter increases at least 10 times.

DETAILED DESCRIPTION OF THE INVENTION

Definitions

Technical terms or scientific terms used herein have definitions as understood by those having an ordinary skill in the art, unless stated otherwise.

Any tools, equipment, methods, or chemicals mentioned here mean tools, equipment, methods, or chemicals commonly operated or used by those skilled in the art, unless explicated stated otherwise that they are tools, equipment, methods, or chemicals specifically used in this invention.

Use of singular noun or singular pronoun with "comprising" in the claims or the specification refers to "one" and also "one or more", "at least one", and "one or more than one".

Throughout this application, the term "about" is used to indicate that any value presented or showed herein may potentially vary or deviate. Such variation or deviation may result from errors of equipment, method, or from individual operator implementing equipment or method. These variations or deviations caused by the changes of physical properties.

"Microaerobic condition" means condition that air has been controlled to be limited without further adding of any gas, including air or inert gas to evacuate the existing air.

"Concentration of carbon source" unless stated specifically, means the concentration of carbon source in such system such as in a fermenter at a specific time.

Hereafter, invention embodiments are shown without any purpose to limit the scope of the invention.

This invention relates to the process for producing lactic acid or its salts from fermentation using thermotolerance *Bacillus* bacteria. Said process comprising the following steps:

(a) cultivating thermotolerance *Bacillus* bacteria to obtain a seed culture;

(b) increasing cell number of bacteria by inoculating the seed culture obtained from step (a) into a fermenter containing an initial carbon source under an aerobic condition;

(c) fermenting the seed culture obtained from step (b) in the fermenter under a microaerobic condition to obtain lactic acid or its salts;

wherein the step (b) comprising at least one addition of the carbon source under any one of the following conditions, which are independent to each other, to increase a concentration of carbon source:
  when the concentration of the carbon source in the fermenter reduces to 50% or less comparing to the initial concentration;
  when the step (b) is carried out for a time of at least one third;
  when an optical density (OD) of bacterial cell in the fermenter increases at least 10 times.

In one embodiment, the addition of carbon source in step (b) in any above conditions increases the concentration of the carbon source in the fermenter to 75% or more comparing to the initial concentration. The addition of said carbon source includes the addition that results in the concentration larger than the initial concentration.

Preferably, the addition of carbon source is performed under the condition that the concentration of the carbon source in the fermenter reduces to 25% or less comparing to the initial concentration.

Preferably, the addition of the carbon source is performed under the step (b) is carried out for the time of at least one half.

Preferably, the addition of the carbon source is performed under the condition that the optical density (OD) of bacteria cell in the fermenter increases at least 10 to 50 times.

In one embodiment, the concentration of the initial carbon source in step (b) may be in a range of 10 to 20 g/L, preferably about 15 g/L.

In one embodiment, said process for producing lactic acid or its salts may be carried out at the temperature in a range of about 45 to about 60° C., preferably at the temperature about 48 to 52° C.

In one embodiment, the thermotolerance *Bacillus* genus in the step (a) may be selected from *Bacillus acidiproducens, Bacillus coagulans*, or a mixture of these bacteria.

In one embodiment, the initial optical density of bacteria cell in the step (a) is about 0.20 to 0.70, preferably 0.20 to 0.40.

In one embodiment, the step (a) may be carried out for about 2 to 5 hours, preferably about 3 to 4 hours.

In one embodiment, a bacteria cultivation media may contain nitrogen source that may be selected from yeast extract, peptone extract, beef extract and legume extract.

In one embodiment, the bacteria cultivation media and bacteria cell increasing media may contain inorganic nitrogen source that may be selected from ammonium chloride, ammonium nitrate, and ammonium dihydrogen phosphate. The use of said inorganic compounds for nitrogen source has benefit in the production of lactic acid in industrial scale because they are cheap, affordable, and can be quality controlled.

In one embodiment, the step (b) may be carried out for about 2 to 5 hours, preferably about 3 to 4 hours, and most preferably about 4 hours.

In one embodiment, the step (c) further comprises at least one addition of the carbon source.

In one embodiment, the concentration of carbon source in step (c) may be in a range of about 100 to 200 g/L, preferably about 100 g/L.

In one embodiment, the step (c) is controlled to have pH of 6 to 7 with a use of basic solution, preferably have pH of 6.5 with a use of basic solution.

In one embodiment, the basic solution may be selected from sodium hydroxide (NaOH), ammonium hydroxide ($NH_4OH$), potassium hydroxide (KOH), or a mixture thereof, preferably sodium hydroxide or potassium hydroxide, and most preferably sodium hydroxide.

In one embodiment, the carbon source used in the production of lactic acid or its salt is a fermentable sugar.

The fermentable sugar is any sugar that can be found in nature or any sugar derived from a substance comprising sugar. Said sugar may be modified or unmodified.

The fermentable sugar may be selected from, but not limited to monosaccharide, disaccharide, trisaccharide, or a mixture thereof.

In one embodiment, the monosaccharide may be selected from glucose, fructose, galactose, or a mixture thereof.

In one embodiment, the disaccharide may be selected from sucrose, lactose, maltose, cellobiose, or a mixture thereof.

In one embodiment, the trisaccharide may be selected from raffinose, isomaltotriose, maltotriose, nigerotriose, kestose, or a mixture thereof.

Preferably, the fermentable sugar is glucose.

In one embodiment, the fermenter in step (b) and/or step (c) further comprises a mixer.

In one embodiment, the mixer has a speed in a range of about 150 to 450 rpm, preferably about 300 rpm.

In one embodiment, the change of fermenter condition from aerobic condition in step (b) to microaerobic condition in step (c) may be performed by stopping aeration in the fermenter in order that the remaining air from step (b) has been consumed, or adding nitrogen to replace air during fermentation in step (c).

In one embodiment, the fermentation in step (c) may be performed in batch, semi-batch, or continuous.

In another embodiment, said production of lactic acid or its salt may further comprises the step of separating and purifying the mixture obtained from step (c).

The separation and purification may be selected from, but not limited to centrifugation, filtration, membrane filtration, flocculation, extraction, distillation, crystallization, filtration, ion exchange resin, or electrodialysis.

The following is the property testing according to the invention, wherein the methods and equipment used in the test are commonly used methods and are not intended to limit the scope of the invention.

Glucose and lactic acid are analyzed by high performance liquid chromatography using a Shimadzu equipped with Biorad, Aminex HPX-87H ion exclusion organic acid (300 mm×7.8 mm) at a temperature around 45° C., and reflective index detector Shimadzu-RID-10A for detecting a signal comparing to a standard signal.

Optical density (OD) of bacteria during cultivation and fermentation is analyzed by spectrophotometry at a wavelength 600 nm.

Yield is calculated from a ratio of an amount of produced lactic acid to an amount of carbon source used during fermentation.

Yield of produced lactic acid per bacteria cell ($Y_{p/x}$) represents the effectiveness of bacteria cell in the production of lactic acid, which is calculated from a ratio of an amount of produced lactic acid and a difference between the bacteria optical density after fermentation step and after increasing of bacteria cell step.

The following examples are presented to illustrate the present invention without limiting the scope of the invention.

In the following examples, unless stated specifically, media for culturing bacteria and increasing bacteria cell has composition (per liter) as following: 10 g glucose, 15 g yeast extract, 4 g ammonium chloride ($NH_4Cl$), 5 g calcium hydroxide ($Ca(OH)_2$), and 20 mL saline solution.

Multiple Additions of the Carbon Source in the Step of Increasing Bacteria Cell

To study the effect of multiple additions of carbon source in the step of increasing bacteria cell on lactic acid or its salt production, a sample without adding carbon source in the step of increasing bacteria cell is used to compare with lactic acid production according to the invention.

Comparative Example (without Adding the Carbon Source in the Step of Increasing Bacteria Cell)

The cultivation of bacteria is carried out by adding thermotolerance *Bacillus* genus in a flask containing bacteria culturing media, wherein the initial concentration of bacteria is about 1% by volume and the initial optical density is about 0.30-0.40. The sample is centrifuged at about 250 rpm for 3 hours at a temperature of about 50° C. to obtain a seed culture. Then, bacteria cell is increased by adding the seed culture in a 5 L fermenter containing about 2.5 L culture media with initial glucose concentration of about 15 g/L and calcium hydroxide ($Ca(OH)_2$) to control pH to be about 6.5. The step of increasing bacteria cell is performed at the temperature about 50° C. for about 3 hours under 1 vvm aeration and 300 rpm mixing. Then, the aeration is stopped and about 1 L of 350 g/L glucose solution is added into the fermenter in order to achieve the initial glucose concentration of 100 g/L at the beginning of the fermentation step. The fermentation is operated under a microaerobic condition at the temperature of about 50° C. and the mixing speed of about 300 rpm by using various basic solutions in Table 1 to control pH to be about 6.5. The fermentation is performed until glucose is not detected. Then, the products are centrifuged at about 10,000 rpm for about 5 minutes. The obtained products are analyzed for produced lactic acid and the optical density of bacteria during fermentation.

Examples According to the Invention

The thermotolerance *Bacillus* genus is added into a flask containing bacteria culturing media, wherein the initial concentration of bacteria is about 1% by volume and the initial optical density is about 0.30-0.40. The sample is centrifuged at about 250 rpm for 3 hours at a temperature of about 50° C. to obtain a seed culture. Then, bacterial cell is increased by adding the seed culture in a 5 L fermenter containing about 2.5 L culture media with initial glucose concentration of about 15 g/L and calcium hydroxide ($Ca(OH)_2$) to control pH to be about 6.5. The step of increasing bacteria cell is performed at the temperature about 50° C. for about 2 hours under 1 vvm aeration and 300 rpm mixing. Then, about 0.5 L of 90 g/L glucose solution was added. The step of increasing bacteria cell is operated for another 2 hours. Then, the fermentation is performed under a microaerobic condition at the temperature of about 50° C. and the mixing speed of about 300 rpm by using various basic solutions in Table 1 to control pH to be about 6.5. The fermentation is performed until glucose is not detected. Then, the products are centrifuged at about 10,000 rpm for about 5 minutes. The obtained products are analyzed for produced lactic acid and the optical density of bacteria during fermentation.

From Table 1, when comparing examples A1, A2, A3 to comparative examples 1a, 2a, and 3a, respectively which are the lactic acid production by using *Bacillus acidiproducens* strain, it can be found that the step of increasing bacteria cell comprising at least one addition of the carbon source results in the higher $Y_{p/x}$, productivity, and yield. Moreover, it can be found that the lactic acid production according to the invention can use sodium hydroxide and potassium hydroxide solutions which are strong acids to control pH during fermentation and gives rise to high lactic acid yield.

Furthermore, when comparing examples B1, B2, B3 to comparative examples 1b, 2b, and 3b, respectively which are the lactic acid production by using *Bacillus coagulans* strain, it can be observed that at least one addition of the carbon source in the step of increasing bacteria cell results in greatly higher $Y_{p/x}$. This indicates an increase of efficiency in utilizing carbon source.

Therefore, regarding above results, it can be summarized that the lactic acid production according to the invention can enhance the efficiency of lactic acid production from thermotolerance *Bacillus* genus, which can be performed easily and can reduce complicated steps as indicated in the objective of this invention.

TABLE 1

The lactic acid bacteria production from thermotolerance *Bacillus* genus in various conditions

| Example | Basic solution in fermentation step | Fermentation period (hr) | Optical density (OD) before the step of increasing bacteria cell | Optical density (OD) after the step of increasing bacteria cell | Optical density (OD) after fermentation | Lactic acid concentration (g/L) | Yield (g/g) | Productivity (g/L/hr) | $Y_{p/x}$ |
|---|---|---|---|---|---|---|---|---|---|
| *Bacillus acidiproducens* strain | | | | | | | | | |
| Comparative Example 1a | 7M NH₄OH | 17 | 0.32 | 7.7 | 20.7 | 87.3 | 0.87 | 5.1 | 6.7 |
| Comparative Example 2a | 10M NaOH | 19 | 0.32 | 7.0 | 22.0 | 99.9 | 0.94 | 5.6 | 6.6 |
| Comparative Example 3a | 10M KOH | 18 | 0.30 | 11.4 | 25.1 | 102.9 | 0.95 | 5.7 | 7.5 |
| Example A1 | 7M NH₄OH | 17 | 0.28 | 10.0 | 21.1 | 99.1 | 0.99 | 5.9 | 8.2 |
| Example A2 | 10M NaOH | 18 | 0.35 | 11.3 | 22.6 | 108.9 | 1.04 | 6.1 | 8.8 |
| Example A3 | 10M KOH | 19 | 0.31 | 12.5 | 23.7 | 102.0 | 0.92 | 5.5 | 9.1 |
| *Bacillus coagulans* strain | | | | | | | | | |
| Comparative Example 1b | 7M NH₄OH | 18 | 0.31 | 9.3 | 21.9 | 93.5 | 0.90 | 5.2 | 7.4 |
| Comparative Example 2b | 10M NaOH | 12 | 0.32 | 10.4 | 20.4 | 94.4 | 0.94 | 7.9 | 9.4 |
| Comparative Example 3b | 10M KOH | 18 | 0.32 | 9.0 | 21.6 | 102.6 | 1.00 | 5.7 | 8.1 |
| Example B1 | 7M NH₄OH | 20 | 0.31 | 13.6 | 28.3 | 102.8 | 1.00 | 5.1 | 6.9 |
| Example B2 | 10M NaOH | 20 | 0.38 | 10.9 | 17.2 | 108.0 | 1.00 | 5.4 | 17.5 |
| Example B3 | 10M KOH | 20 | 0.26 | 9.5 | 16.5 | 102.9 | 0.97 | 5.2 | 14.7 |

BEST MODE OF THE INVENTION

Best mode of the invention is as disclosed in the detailed description.

The invention claimed is:

1. A process for producing lactic acid or its salts, comprising the steps of:
   (a) cultivating thermotolerant *Bacillus* genus bacteria to obtain a seed culture having an initial optical density (OD);
   (b) increasing the cell number of the thermotolerant *Bacillus* genus bacteria by inoculating the seed culture obtained from step (a) into a fermenter containing an initial carbon source at an initial concentration under an aerobic condition for a period of time;
   (c) fermenting the seed culture obtained from step (b) in the fermenter under a microaerobic condition to obtain lactic acid or its salts;
   wherein step (b) further comprises at least one addition of the carbon source under any one of the following conditions, which are independent of each other, to increase the concentration of the carbon source:
   when the concentration of the carbon source in the fermenter reduces to 50% or less compared to the initial concentration;
   when step (b) is carried out after at least one third (⅓) of the said period of time has elapsed;
   when the optical density (OD) of bacteria cells in the fermenter increases by at least 10 times compared to the initial optical density (OD).

2. The process for producing lactic acid or its salts according to claim 1, wherein the addition of the carbon source in step (b) increases the concentration of the carbon source in the fermenter to 75% or more compared to the initial concentration.

3. The process for producing lactic acid or its salts according to claim 1, wherein the addition of the carbon source in step (b) is performed under the condition that the concentration of the carbon source in the fermenter reduces to 25% or less compared to the initial concentration.

4. The process for producing lactic acid or its salts according to claim 1, wherein the addition of the carbon source is performed under the condition that step (b) is carried out after at least one half (½) of the said period of time has elapsed.

5. The process for producing lactic acid or its salts according to claim 1, wherein the addition of the carbon source is performed under the condition that the optical density (OD) of bacteria cells in the fermenter increases by 10 to 50 times compared to the initial optical density (OD).

6. The process for producing lactic acid or its salts according to claim 1, wherein the concentration of the initial carbon source in step (b) is in a range of from 10 to 20 g/L.

7. The process for producing lactic acid or its salts according to claim 1, wherein the concentration of the initial carbon source in step (b) is 15 g/L.

8. The process for producing lactic acid or its salts according to claim 1, wherein said process is carried out at a temperature in a range of from 45 to 60° C.

9. The process for producing lactic acid or its salts according to claim 8, wherein said process is carried out at the temperature in the range of from 48 to 52° C.

10. The process for producing lactic acid or its salts according to claim 1, wherein the thermotolerant *Bacillus* genus bacteria in step (a) is selected from *Bacillus acidiproducens*, *Bacillus coagulans*, or a mixture of these bacteria.

11. The process for producing lactic acid or its salts according to claim 1, wherein step (a) is carried out for 2 to 5 hours.

12. The process for producing lactic acid or its salts according to claim 11, wherein step (a) is carried out for 3 to 4 hours.

13. The process for producing lactic acid or its salts according to claim 1, wherein step (b) is carried out for 2 to 5 hours.

14. The process for producing lactic acid or its salts according to claim 13, wherein step (b) is carried out for 3 to 4 hours.

15. The process for producing lactic acid or its salts according to claim 14, wherein step (b) is carried out for 4 hours.

16. The process for producing lactic acid or its salts according to claim 1, wherein step (c) further comprises at least one addition of the carbon source.

17. The process for producing lactic acid or its salts according to claim 16, wherein the concentration of the carbon source in step (c) is in a range of from 100 to 200 g/L.

18. The process for producing lactic acid or its salts according to claim 17, wherein the concentration of the carbon source in step (c) is 100 g/L.

19. The process for producing lactic acid or its salts according to claim 1, wherein step (c) is controlled so as to have a pH of 6 to 7 with the use of basic solution.

20. The process for producing lactic acid or its salts according to claim 19, wherein step (c) is controlled so as to have a pH of 6.5 with the use of basic solution.

21. The process for producing lactic acid or its salts according to claim 19, wherein the basic solution is selected from sodium hydroxide, ammonium hydroxide, potassium hydroxide, or a mixture thereof.

22. The process for producing lactic acid or its salts according to claim 21, wherein the basic solution is sodium hydroxide or potassium hydroxide.

23. The process for producing lactic acid or its salts according to claim 22, wherein the basic solution is sodium hydroxide.

24. The process for producing lactic acid or its salts according to claim 1, wherein the carbon source is a fermentable sugar.

25. The process for producing lactic acid or its salts according to claim 24, wherein the fermentable sugar is selected from monosaccharide, disaccharide, trisaccharide, or a mixture thereof.

26. The process for producing lactic acid or its salts according to claim 25, wherein the monosaccharide is selected from glucose, fructose, galactose, or a mixture thereof.

27. The process for producing lactic acid or its salts according to claim 25, wherein the disaccharide is selected from sucrose, lactose, maltose, cellobiose, or a mixture thereof.

28. The process for producing lactic acid or its salts according to claim 25, wherein the trisaccharide is selected from raffinose, isomaltotriose, rnaltotriose, nigerotriose, kestose, or a mixture thereof.

29. The process for producing lactic acid or its salts according to claim 24, wherein the fermentable sugar is glucose.

30. The process for producing lactic acid or its salts according to claim 1, wherein the fermenter further comprises a mixer.

31. The process for producing lactic acid or its salts according to claim 30, wherein the mixer has a speed in a range of from 150 to 450 rpm.

32. The process for producing lactic acid or its salts according to claim 31, wherein the mixer has a speed of 300 rpm.

33. The process for producing lactic acid or its salts according to claim 2, wherein the addition of the carbon source in step (b) is performed under the condition that the concentration of the carbon source in the fermenter reduces to 25% or less compared to the initial concentration.

34. The process for producing lactic acid or its salts according to claim 2, wherein the addition of the carbon source is performed under the condition that step (b) is carried out after at least one half (½) of the said period of time has elapsed.

35. The process for producing lactic acid or its salts according to claim 2, wherein the addition of the carbon source is performed under the condition that the optical density (OD) of bacteria cells in the fermenter increases by 10 to 50 times compared to the initial optical density (OD).

36. The process for producing lactic acid or its salts according to claim 6, wherein the concentration of the initial carbon source in step (b) is 15 g/L.

37. The process for producing lactic acid or its salts according to claim 10, wherein step (a) is carried out for 2 to 5 hours.

38. The process for producing lactic acid or its salts according to claim 16, wherein the concentration of the carbon source in step (c) is in a range of from 100 to 200 g/L.

\* \* \* \* \*